US006782895B2

(12) United States Patent
Van Nguyen et al.

(10) Patent No.: US 6,782,895 B2
(45) Date of Patent: Aug. 31, 2004

(54) COMPOSITIONS COMPRISING AT LEAST ONE HYDROXIDE COMPOUND AND AT LEAST ONE COMPLEXING AGENT, AND METHODS FOR USING THE SAME

(75) Inventors: Nghi Van Nguyen, Edison, NJ (US); David W. Cannell, Plainfield, NJ (US)

(73) Assignee: L'Oreal, S.A., Paris (FR)

( * ) Notice: Subject to any disclaimer, the term of this patent is extended or adjusted under 35 U.S.C. 154(b) by 128 days.

(21) Appl. No.: 09/931,914

(22) Filed: Aug. 20, 2001

(65) Prior Publication Data

US 2003/0079299 A1 May 1, 2003

(51) Int. Cl.$^7$ ................................................ A45D 7/04
(52) U.S. Cl. ..................... 132/203; 132/202; 132/204; 132/205; 132/206; 132/207
(58) Field of Search ................................ 132/203, 202, 132/204, 205, 206, 207

(56) References Cited

U.S. PATENT DOCUMENTS

| | | | |
|---|---|---|---|
| 4,509,983 A | 4/1985 | Szabó et al. | 106/38.2 |
| 4,783,395 A | 11/1988 | Hsieh et al. | 524/320 |
| 4,816,246 A | 3/1989 | Mathews et al. | 424/72 |
| 4,898,726 A | 2/1990 | Beste | 424/72 |
| 4,992,267 A | 2/1991 | DenBeste et al. | 424/71 |
| 5,332,570 A | 7/1994 | Bergstrom et al. | 424/72 |
| 5,641,477 A | 6/1997 | Syed et al. | 424/70.4 |
| 6,058,943 A | 5/2000 | Davis-Harris | 132/205 |
| 6,287,582 B1 * | 9/2001 | Gott et al. | 424/402 |
| 6,435,193 B1 * | 8/2002 | Cannell et al. | 132/203 |

FOREIGN PATENT DOCUMENTS

WO    WO 01/64171    9/2001

OTHER PUBLICATIONS

S. Ogawa et al. *A curing method for permanent hair straightening using thioglycolic and dithiodiglycolic acids, Journal of Cosmetic Science*, 51, 379–399 (Nov./Dec. 2000).

Co–pending application No. 09/789,667 –Title: Hair Relaxer Compositions Comprising at Least One Hydroxide Compound and at Least One Activating Agent, and Methods of Using the Same Inventors: David W. Cannell et al. U.S. Filing Date: Feb. 22, 2001.

Co–pending application No. 09/516,942 –Title: Hair Relaxer Compositions Utilizing Complexing Agent Activators Inventors: Nghi Van Nguyen et al. U.S. Filing Date: Mar. 1, 2000.

Co–pending application No. 09/931,919 –Title: Method for Relaxing and Re–Waving Hair Comprising at Least One Reducing Agent and at Least One Hydroxide Compound Inventors: David W. Cannell et al. U.S. Filing Date: Apr. 20, 2001.

Co–pending application No. 09/838,197 –Title: Composition and Methods for Lanthionizing Keratin Fibers Using at Least One Organic Nucleophile and at Least One Hydroxide Ion Generator Inventors: David W. Cannell et al. U.S. Filing Date: Apr. 20, 2001.

Co–pending application No. 09/717,206 –Title: Hair Relaxer Compositions Utilizing Cation Exchange Compositions Inventors: David W. Cannell et al. U.S. Filing Date: Nov. 22, 2001.

Co–pending application No. 09/931,913 –Title: Compositions Comprising at Least One Hydroxide Compound and at Least One Oxidizing Agent, and Methods to Straighten Curly Hair Inventors: Nghi Van Nguyen et al. U.S. Filing Date: Aug. 20, 2001.

Co–pending application No. 09/931,912 –Title: Compositions Comprising at Least One Hydroxide Compound and at Least One Reducing Agent, and Methods for Relaxing Inventors: Nghi Van Nguyen et al. U.S. Filing Date: Aug. 20, 2001.

Derwent Abstract of JP 2000–170094.

Derwent Abstract of J60021704.

Zahn, H., *N,O–peptidylverschiebung, Disulfidaustauch und Lanthioninbildung in Wolle under anderen cystinhaltigen Proteinen*, Chimia, Aarua, Ch, No. 15, Jul. 1961, pp. 378–394.

Copy of International Search Report dated Nov. 8, 2002.

\* cited by examiner

*Primary Examiner*—Brian P. Mruck
*Assistant Examiner*—Eisa Elhilo
(74) *Attorney, Agent, or Firm*—Finnegan, Henderson, Farabow, Garrett & Dunner LLP

(57) ABSTRACT

A composition comprising at least one hydroxide compound and at least one complexing agent effective for dissociating the at least one hydroxide compound in sufficient quantity to effect lanthionization of keratin fibers. The at least one complexing agent is chosen from compounds comprising at least one group of formula (I) and salts thereof. Also disclosed is a method for lanthionizing keratin fibers to achieve relaxation of the keratinous fibers and a multicompartment kit comprising an activating composition and at least one hydroxide compound.

36 Claims, No Drawings

COMPOSITIONS COMPRISING AT LEAST ONE HYDROXIDE COMPOUND AND AT LEAST ONE COMPLEXING AGENT, AND METHODS FOR USING THE SAME

The present invention relates to compositions and methods for lanthionizing keratin fibers using a combination of at least one hydroxide compound and at least one complexing agent effective for dissociating the at least one hydroxide compound in sufficient quantity to effect lanthionization of the keratin fibers. The at least one complexing agent comprises at least one group chosen from groups of formula (I) as defined below and salts thereof.

Straightening or relaxing the curls of very curly hair may increase the manageability and the ease of styling such hair. In today's market, there is an increasing demand for hair care products referred to as "hair relaxers" which can relax or straighten naturally curly or kinky hair. Hair relaxers may either be applied in a hair salon by a professional or in the home by the individual consumer.

Hair fiber is a keratinous material which is comprised of proteins. Many of the polypeptides in hair fibers are bonded together by disulfide bonds (—S—S—). A disulfide bond may be formed from the reaction of the two sulfhydryl groups (—SH) one on each of two cysteine residues which results in the formation of a cystine residue. While there may be other types of bonds between the polypeptides in hair fibers, such as ionic bonds, the permanent curling and the shape of the hair is essentially dependent on the disulfide bonds of cystine residues.

Generally, hair relaxing processes are chemical processes which may alter the aforementioned disulfide bonds between polypeptides in hair fibers and may form lanthionine residues $[S[CH_2CH(NH-)(CO-)]_2]$. Thus, the term "lanthionizing" is used when one skilled in the art refers to the relaxing of keratin fibers by hydroxide ions. "Lanthionizing," as used herein, refers to the formation of at least one lanthionine residue, which may accomplish, for example, any level of relaxation. "Relaxation" and "relaxing," as used herein, includes any level of relaxing, for example, from slight relaxing to straightening.

For example, hair fibers may be relaxed or straightened by disrupting the disulfide bonds of the hair fibers with an alkaline reducing agent. The chemical disruption of disulfide bonds with such an agent is generally combined with mechanical straightening of the hair, such as combing, and straightening generally occurs due to changes in the relative positions of neighboring polypeptide chains within the hair fiber. This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. One reaction sequence comprises at least one bimolecular nucleophilic substitution reaction wherein an available hydroxide ion directly attacks the disulfide linkage of a cystine residue. The result is the formation of lanthionine residues and $HOS^-$. See Zviak, C., *The Science of Hair Care*, 185–186 (1986). The second reaction sequence comprises at least one β-elimination reaction initiated by the nucleophilic attack of an available hydroxide ion on a hydrogen atom bonded to a carbon atom that is in the β-position with respect to the disulfide bond of a cystine residue. See Zviak. The result is the formation of a dehydroalanine residue. The dehydroalanine residue then reacts with either the thiol group of a cysteine residue or the amino group of an alanine residue to form a lanthionine residue or a lysinoalanine residue, respectively. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid or minimize damage to the hair protein or skin. If such a step is required, an acidic shampoo may be used to neutralize residual alkali and remove it from the hair and scalp.

Relaxing compositions are generally in the form of gels or emulsions that contain varying proportions of strong bases that are water soluble, such as sodium hydroxide, or compositions that contain slightly soluble metal hydroxides, e.g., calcium hydroxide ($Ca(OH)_2$), that are converted in situ to soluble bases, e.g., guanidine hydroxide. Traditionally, the two main technologies used in the hair care industry for generating hydroxide ions to relax keratin fibers are referred to as "lye" (lye=sodium hydroxide) relaxers and "no lye" relaxers. The "lye" relaxers use sodium hydroxide in a concentration generally ranging from 1.5% to 2.5% by weight relative to the total weight of the composition (0.38–0.63 M) depending on the base or carrier used, the condition of the hair fibers, and the desired length of the relaxation process. Sodium hydroxide may be extremely effective in straightening the hair but may result in a reduction in strength of the hair fibers and, in some cases, partial or total loss of hair due to hair fiber breakage. Some manufacturers market lithium and potassium hydroxide relaxers as "no lye" but, while this is technically true, these relaxers still rely on the soluble hydroxides of the inorganic potassium or lithium.

Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

Guanidine carbonate and calcium hydroxide, however, create a different set of problems. The insoluble byproduct, $CaCO_3$, leaves a white residue or unattractive "whitening" or "ashing" that remains in the hair since divalent metals like calcium have a relatively good affinity to keratin. A decalcifying shampoo is subsequently needed to remove the ashing.

Thus, there is still a need for a process to relax keratin fibers that has the advantages of using an insoluble or partially soluble metal hydroxide, such as $Ca(OH)_2$, but reduces or eliminates the problem of ashing caused by the insoluble byproduct, $CaCO_3$.

The present invention provides a method for lanthionizing keratin fibers comprising generating hydroxide ions in a composition, said step of generating comprising combining (i) at least one hydroxide composition comprising at least one hydroxide compound and (ii) at least one an activating composition comprising at least one complexing agent effective for dissociating the at least one hydroxide compound in sufficient quantity to effect lanthionization of the keratin fibers. The composition comprising the generated hydroxide ions may then be applied to keratin fibers for a sufficient period of time to lanthionize the keratin fibers. Lanthionization may be terminated when a desired level of relaxation of the keratin fibers has been reached. As used herein, "at least one" means one or more and thus includes individual components as well as mixtures/combinations. Further, "keratinous fibers" as defined herein may be human keratinous fibers, and may be chosen from, for example, hair.

According to the present invention the at least one complexing agent comprises at least one group chosen from groups of formula (I) and salts thereof. Formula (I) is defined as

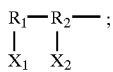  (I)

wherein:
  $R_1$ is chosen from a carbonyl group and a thiocarbonyl group;
  $R_2$ is chosen from CR groups wherein R is chosen from a direct bond to a neighboring atom, H, optionally substituted linear hydrocarbon groups, optionally substituted branched hydrocarbon groups, optionally substituted cyclic hydrocarbon groups, optionally substituted amino groups, optionally substituted thio groups, optionally substituted hydroxy groups, and halogen atoms;
  $X_1$ is chosen from hydroxyl groups and thiol groups; and
  $X_2$ is chosen from hydroxyl groups, amino groups, and thiol groups. For example, when R is a direct bond to a neighboring atom, groups of formula (I) have the following formula:

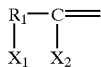

In another embodiment, the present invention is drawn to a composition comprising at least one hydroxide compound and at least one complexing agent effective for dissociating the at least one hydroxide compound in sufficient quantity to effect lanthionization of keratin fibers, wherein the at least one complexing agent comprises at least one group chosen from groups of formula (I) and salts thereof.

Another embodiment of the invention relates to a multi-compartment kit comprising at least two compartments, wherein a first compartment contains a composition for generating hydroxide ions comprising at least one hydroxide compound; and a second compartment contains an activating composition comprising at least one complexing agent effective for dissociating the at least one hydroxide compound in sufficient quantity to effect lanthionization of keratin fibers. The at least one complexing agent comprises at least one group chosen from groups of formula (I) and salts thereof.

It is to be understood that both the foregoing general description and the following detailed description are exemplary and explanatory only and are not restrictive of the invention as claimed. Reference will now be made in detail to exemplary embodiments of the present invention.

Not to be limited as to theory, the lanthionization of keratin fibers is believed to be driven by the release of hydroxide ions, which disrupt the disulfide bonds of cystine. In one embodiment, the compositions of the present invention provide a novel way of generating soluble hydroxide ions from metal hydroxides wherein the soluble hydroxide ions are effective for relaxing hair. As described above, the hair relaxing compositions of the prior art utilized soluble metal hydroxides or slightly soluble metal hydroxides. Slightly soluble metal hydroxides, including most divalent metal hydroxides, are usually not soluble enough in water to generate sufficient soluble hydroxide ions to effect lanthionization of keratin fibers. This can be represented by the following, in which the equilibrium favors the left side of the reaction:

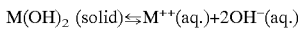

Therefore, in traditional relaxers containing slightly soluble metal hydroxides, the equilibrium was pushed to the right side and the reactions driven to completion by the precipitation of $M^{++}$ as an insoluble compound, such as $CaCO_3$.

The compositions of the present invention, however, in one embodiment, utilize at least one complexing agent to dissociate the at least one hydroxide compound and to chelate and/or sequester $M^{++}$. The at least one complexing agent and the cation may form a complex that, in most cases, has a stronger interaction between the at least one complexing agent and the cation than between the hydroxide ion and the cation. As a result, the at least one complexing agent removes the cation from the above reaction medium and allows the equilibrium to be shifted to the right side. In other words, the at least one complexing agent may help to chelate, sequester or otherwise tie up the cation of the at least one hydroxide compound, allowing more hydroxide ions to be liberated. Thus, the net effect of the use of at least one complexing agent in accord with the present invention may be generation of enough hydroxide ions to effect lanthionization of keratin fibers without relying on the precipitation of the cation. The complexing agent may also be used in combination with precipitation of the cation to generate hydroxide ions.

As described above, the at least one complexing agent according to the present invention comprises at least one group chosen from groups of formula (I) and salts thereof. Non-limiting examples of the R of $R_2$ include linear alkyl groups, branched alkyl groups, cyclic alkyl groups, linear alkylene groups, branched alkylene groups, cyclic alkylene groups, aryl groups, alkyl amino groups, alkylene amino groups, aryl amino groups, mercaptans groups, aryl thiol groups, hydroxyl groups, ether groups, ester groups, keto groups, and carboxyl groups. According to the present invention, R may also optionally be substituted.

Note that as used herein, "hydrocarbon groups" include alkyl groups, alkylene groups, alkenyl groups, and alkenylene groups.

Also note that as used herein, the term "alkyl group" refers to substituted linear alkyl groups, unsubstituted linear alkyl groups, substituted branched alkyl groups, unsubstituted branched alkyl groups, substituted cyclic alkyl groups and unsubstituted cyclic alkyl groups, wherein the alkyl groups comprise at least one carbon and may optionally further comprise at least one heteroatom intercalated in the alkyl chain. Non-limiting examples of alkyl groups include methyl, methyl ethyl ether, and diethyl amine.

Further, as used herein, "alkylene group" refers to substituted linear alkylene groups, unsubstituted linear alkylene groups, substituted branched alkylene groups, unsubstituted branched alkylene groups, substituted cyclic alkylene groups and unsubstituted cyclic alkylene groups, wherein the alkylene groups comprise at least one carbon and may optionally further comprise at least one heteroatom intercalated in the alkylene chain. Similarly, as used herein, the term "alkenyl group" refers to substituted linear alkenyl groups, unsubstituted linear alkenyl groups, substituted branched alkenyl groups, unsubstituted branched alkenyl groups, substituted cyclic alkenyl groups and unsubstituted cyclic alkenyl groups, wherein the alkenyl groups comprise at least one carbon and at least one double bond, and may optionally further comprise at least one heteroatom intercalated in the alkenyl chain.

Further, as used herein, the term "alkenylene group" refers to substituted linear alkenylene groups, unsubstituted linear alkenylene groups, substituted branched alkenylene groups, unsubstituted branched alkenylene groups, substituted cyclic alkenylene groups and unsubstituted cyclic alkenylene groups, wherein the alkenylene groups comprise at least one carbon and at least one double bond, and may optionally further comprise at least one heteroatom intercalated in the alkenylene chain.

As used herein, "substituted" means comprising at least one substituent. Non-limiting examples of substituents include heteroatoms, such as oxygen atoms, sulfur atoms and nitrogen atoms, as well as functional groups, such as thiol groups, hydroxyl groups, ether groups, oxyalkylene groups, polyoxyalkylene groups, carboxylic acid groups, amine groups, amide groups, halogen containing groups, ester groups, siloxane groups, and polysiloxane groups. Thus, as used herein, substituted alkyl groups comprise, for example, hydroxylated alkyl groups (R—OH).

Non-limiting examples of the at least one complexing agent comprising at least one group of formula (I) include α-amino carboxylic acids (such as amino acids), α-hydroxy carboxylic acids (such as aldonic acids and aldaric acids), α-thio carboxylic acids, and α-hydroxy thioacids.

In one embodiment, the at least one complexing agent is chosen from mucic acid wherein mucic acid is optionally substituted; homologs of mucic acid wherein the homologs of mucic acid are optionally substituted; derivatives of mucic acid wherein the derivatives of mucic acid are optionally substituted; and salts of any of the foregoing. Mucic acid is a vegetable-derived polyhydroxy acid. Its chemical name is 1,2,3,4-tetrahydroxy-1,4-butane dicarboxylic acid, and it is manufactured, for example, by Soliance (Route de Bazancourt, F-51110 Pomacle, France) under the name MUCILIANCE. Mucic acid may be obtained by hydrolysis of the pectin contained in vegetable material to yield D-galacturonic acid. The electrochemical oxidation of D-galacturonic acid leads to mucic acid.

Mucic acid in solution exists in equilibrium between its acid form, its δ-lactone form, and its γ-lactone form. The solubility of mucic acid in water varies according to pH. At a pH ranging from 5 to 7, mucic acid is soluble at a concentration ranging from 0.2% to 0.3%. Mucic acid is insoluble in most organic solvents, for example, alcohols and ethers.

The salt form of mucic acid is also not very water-soluble (only about 0.7% of mucic acid dissolves in water at high pH). Moreover, the by-products of mucic acid-metal hydroxide are rather insoluble, e.g., precipitation was observed upon mixing mucic acid sodium salt with calcium hydroxide.

A derivative of mucic acid refers to a mucic acid molecule that is substituted with any substituent at any position of the molecule, provided that the complexing ability of the molecule is not substantially adversely affected. The applicability of a derivative, homolog, etc. of mucic acid may be evaluated, for example, using the procedures of Example 1.

The substitution may occur at any or all of the four carbon atoms of the mucic acid molecule. The hydrogen atom at any carbon atom may be replaced with at least one substituent. Non-limiting examples of substituents include alkyl groups, alkenyl groups, amino groups, amido groups, thiol groups, and alkylthio groups, all of which may optionally be further substituted with at least one substituent.

The at least one complexing agent and the at least one hydroxide compound of the present invention may be present in a molar ratio ranging from 1:0.1 to 1:5 of the at least one complexing agent in the composition to the at least one hydroxide compound in the composition, where "the composition," as used herein, refers to the mixture of the at least one activating composition and the at least one hydroxide composition. In one embodiment, the at least one complexing agent and the at least one hydroxide compound of the present invention may be present in a molar ratio ranging from 1:0.3 to 1:2 of the at least one complexing agent in the composition to the at least one hydroxide compound in the composition. In another embodiment, the at least one complexing agent is present in an amount of 7% by weight relative to the total weight of the composition.

According to the present invention, the at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable. For example, the at least one hydroxide compound can also be chosen from those formed in situ, such as, for example, guanidine hydroxide. As previously mentioned, guanidine hydroxide may be formed in situ, for example, from the reaction of calcium hydroxide and guanidine carbonate. In one embodiment, the at least one hydroxide compound is chosen from calcium hydroxide, barium hydroxide, magnesium hydroxide, aluminum hydroxide, cupric hydroxide, strontium hydroxide, molybdenum hydroxide, manganese hydroxide, zinc hydroxide and cobalt hydroxide. In another embodiment, the at least one hydroxide compound is chosen from calcium hydroxide.

According to the present invention, the at least one hydroxide compound may be present in an amount generally ranging from 0.1% to 10% by weight relative to the total weight of the at least one hydroxide composition, such as from 2% to 5% by weight.

In one embodiment, the at least one activating composition further comprises at least one compound effective for forming at least one salt of the groups of formula (I). A non-limiting example of the at least one compound effective for forming at least one salt of the groups of formula (I) is hydroxide compounds, which may be identical to or different from the at least one hydroxide compound. For example, the at least one compound effective for forming at least one salt of said groups of formula (I) may be chosen from sodium hydroxide, potassium hydroxide and lithium hydroxide. Further for example, the at least one compound effective for forming at least one salt of said groups of formula (I) may be chosen from organic bases. Non-limiting examples of organic bases include compounds comprising at least one quaternary ammonium group, compounds comprising at least one ammonium group, such as ammonium hydroxide, compounds comprising at least one amino group, such as amine bases, and guanidine and derivatives thereof. In one embodiment, the at least one compound effective for forming at least one salt of said groups of formula (I) is chosen from metal hydroxides, such as, for example, sodium hydroxide.

In another embodiment, the at least one activating composition further comprises at least one solvent. Non-limiting examples of the at least one solvent include water and organic solvents, such as DMSO. In one embodiment, the at least one solvent is water.

In yet another embodiment, the at least one activating composition is in the form of a salt slurry. For example, the at least one complexing agent may be a salt, or may be converted to a salt form in order to obtain the salt slurry. This salt slurry may then be mixed with the at least one hydroxide composition comprising the at least one hydroxide compound.

The at least one complexing agent may be converted to a salt form by any method that is capable of converting at least one complexing agent to a salt. For example, the at least one compound effective for forming at least one salt of the groups of formula (I), such as sodium hydroxide, may be added to an aqueous solution of the at least one complexing agent in an amount effective for converting the at least one complexing agent to its salt form.

According to the present invention, the relaxing efficiency of the at least one activating composition, in the form of a salt slurry, may be varied by varying the amount of water in the at least one activating composition. For example, the relaxing efficiency of a mucic acid salt slurry may be increased by increasing the amount of water in the composition.

The compositions of the present invention may be provided as a one-part composition comprising the at least one hydroxide compound and the at least one complexing agent.

The compositions may also be provided in the form of a multicompartment kit. In one embodiment, the multicompartment kit comprises at least two separate components. A first compartment of the kit comprises at least one composition for generating hydroxide ions that comprises at least one hydroxide compound. This first composition may, for example, be in the form of an emulsion, solution, suspension, gel or paste. A second compartment of the kit may comprise at least one activating composition comprising at least one complexing agent comprising at least one group chosen from groups of formula (I) and salts thereof, effective for dissociating the at least one hydroxide compound in sufficient quantity to effect lanthionization of keratin fibers. This second compartment may, for example, be in the form of an emulsion, solution, suspension, gel or paste. The skilled artisan, based on the stability of the composition and the application envisaged, will be able to determine how the composition and/or multicompartment compositions should be stored and mixed.

According to one embodiment of the invention, at least one compartment of the multicompartment kit will contains enough of at least one solvent to ensure that, upon mixing, enough of the generated hydroxide ions remain in solution to effect lanthionization of keratin fibers.

The at least one solvent useful in the present invention, in one embodiment, is a solvent that lowers the ionic bonding forces in the solute molecule enough to cause separation of the constituent ions. In one embodiment, the at least one solvent is chosen from water and organic solvents, such as dimethyl sulfoxide (DMSO).

The present invention also provides for a simple screening test, which may be used to determine the applicability of a complexing agent for use as the at least one complexing agent in the lanthionizing compositions of the present invention. By titrating a suspension of a hydroxide compound, such as $Ca(OH)_2$, with the complexing agent of interest, the chelating or sequestering properties may be observed. If the solution reaches a pH sufficient for lanthionizing keratin fibers, then the complexing agent is a good candidate for use as the at least one complexing agent of the present invention.

The compositions of the present invention may further comprise at least one suitable additive chosen from additives commonly used in hair relaxing compositions. Non-limiting examples of the at least one suitable additive include dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, synthetic oils and any other additive conventionally used in compositions for the care and/or treatment of hair.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis.

EXAMPLES

Example 1

Complexing of Solid $Ca(OH)_2$ with $Na_4EDTA$

A screening test to determine the applicability of a complexing agent for use in the lanthionizing compositions of the present invention was carried out. For the purpose of demonstrating the application of this screening test, $Na_4EDTA$ is employed as a complexing agent.

A solution of the complexing agent, 3 g of VERSENE 220 (tetrasodium EDTA ($Na_4EDTA$), 0.0066 moles) in 97 g of water, was titrated with the multivalent metal hydroxide solid, $Ca(OH)_2$. At the end of the reaction, 0.60 g of $Ca(OH)_2$ had been dissolved in the solution. Since the known solubility of $Ca(OH)_2$ is 0.15 g/100 ml of water, the amount of $Ca(OH)_2$ further dissolved in the solution due to the chelation of $Na_4EDTA$ was 0.45 g or 0.0061 moles. The results are shown in Table 1.

Tetrasodium EDTA was a strong calcium binding constant in the high alkaline range. The results demonstrated that the complexing process occurs up to a 1:1 molar ratio of the complexing agent:metal hydroxide. The result was that the total chelation of $Ca(OH)_2$ by $Na_4EDTA$ at 1:1 molar ratio and the release of hydroxide ions to the solution. Since the solution reached a pH sufficient for lanthionizing keratin fibers, tetrasodium EDTA is shown to be an effective complexing agent.

TABLE 1

Ca(OH)₂ Solubilized by EDTA

| Amount of Ca(OH)₂ added (gram) | pH | Appearance |
| --- | --- | --- |
| 0 | 11.62 | Clear |
| 0.20 | 13.32 | Clear |
| 0.40 | 13.52 | Clear |
| 0.60 | 13.59 | Clear |
| 0.65 | 13.63 | Cloudy |

Example 2
Generation of Hydroxide Ions from the Reaction of Mucic Acid and Calcium Hydroxide To a solution of 7 g mucic acid (0.0333 moles) was added 2.66 g (0.066 moles) of sodium hydroxide. An incremental amount of calcium hydroxide was then added slowly to the slurry of mucic acid sodium salt, and the pH was measured. The results are shown in Table 2.

TABLE 2

The Relationship between pH and Amount of Ca(OH)₂

| Calcium Hydroxide Added | pH |
| --- | --- |
| 0.0 g | 12.39 |
| 0.2 g | 13.02 |
| 0.4 g | 13.32 |
| 0.6 g | 13.46 |
| 0.8 g | 13.51 |
| 1.0 g | 13.53 |
| 1.2 g | 13.55 |

The results indicate that hydroxide ions were generated when the insoluble calcium hydroxide was added to the mucic acid sodium salt slurry.

Example 3
Procedure for Measuring Relaxing Efficiency

A naturally kinky hair swatch was relaxed using a composition comprising at least one hydroxide composition comprising at least one hydroxide compound and at least one activating composition comprising at least one complexing agent according to the present invention. The relaxed hair swatch was then rinsed, shampooed, and then placed in the humidity chamber at 90% Relative Humidity (% RH) for 24 hours. The percent Relaxing Efficiency (% RE) is defined as:

% RE=($L_f/L_t$)×100

$L_f$=length of the relaxed hair after 24 hours at 90% RH
$L_t$=length of the hair at the straight configuration The following examples illustrate the method of using this new composition to straighten kinky hair.

Effectiveness of Mucic Acid in a Hair Relaxer

Mucic acid in 3 g of water was converted to its sodium salt by reacting with an appropriate amount of sodium hydroxide. This mucic acid sodium salt slurry was mixed with 6 g of a 7% calcium hydroxide cream. The calcium hydroxide cream contained the following ingredients by weight, relative to the total weight of the cream:

| Materials | % w/w |
| --- | --- |
| Cetyl alcohol | 1.0 |
| Steareth-2 | 0.5 |
| Steareth-10 | 2.5 |
| Mineral oil | 15.0 |
| Petrolatum | 5.5 |
| Cetearyl alcohol and cetearyl phosphate | 7.5 |
| Propylene glycol | 3.0 |
| Calcium hydroxide | 7.0 |
| Water | 58.0 |

The mixture of mucic acid sodium salt slurry and calcium hydroxide cream was applied to naturally kinky hair for 30 minutes. The treated hair was shampooed and then placed in a humidity chamber at 90% RH for 24 hours. The % RE is shown in Table 3.

TABLE 3

Relaxing Efficiency of Hair Treated with Mucic Acid and Calcium Hydroxide at Various Molar Ratios of Calcium Hydroxide: Mucic Acid

| Ca(OH)₂ Cream | Mucic Acid | 50% NaOH | Water | Molar Ratio | % RE |
| --- | --- | --- | --- | --- | --- |
| 6 g | 1.19 g | 0.9 g | 3 g | 1:1 | 21 |
| 6 g | 0.84 g | 0.64 g | 3 g | 1:0.7 | 86 |
| 6 g | 0.60 g | 0.46 g | 3 g | 1:0.5 | 80 |
| 6 g | 0.48 g | 0.37 g | 3 g | 1:0.4 | 81 |
| 6 g | 0.36 g | 0.27 g | 3 g | 1:0.3 | 54 |

The results indicate that mucic acid can be used with calcium hydroxide to relax naturally kinky hair.

Example 4
Effects of Water in Mucic Acid-Calcium Hydroxide Relaxer

Since the mucic acid sodium salt has limited solubility in water, additional water would increase the relaxing efficiency. Curly hair was treated with a slurry of mucic acid sodium salt with various amounts of water and 6 g of a 7% calcium hydroxide cream (see Example 3) (1:0.7 molar ratio of calcium hydroxide:mucic acid). The %RE are shown in Table 4.

TABLE 4

Relaxing Efficiency of Hair Relaxed with Mucic Acid and Calcium Hydroxide

| Amount of Water in Mucic Acid Salt Slurry | % RE |
| --- | --- |
| 2 g | 42 |
| 3 g | 88 |
| 4 g | 95 |
| 5 g | 98 |
| 6 g | 99 |

The results indicate that as the availability of mucic acid salt increased, more hydroxide ions were generated, resulting in a higher relaxing efficiency.

What is claimed is:

1. A method for lanthionizing keratin fibers comprising
   (a) generating hydroxide ions in a composition, said step of generating comprising combining:
      (i) at least one hydroxide composition comprising at least one hydroxide compound; and
      (ii) at least one activating composition comprising at least one complexing agent effective for dissociating said at least one hydroxide compound in sufficient quantity to effect lanthionization of said keratin fibers;

(b) applying said composition comprising said generated hydroxide ions to keratin fibers for a sufficient period of time to lanthionize said keratin fibers; and (c) terminating said lanthionization, wherein said at least one complexing agent comprises at least one group chosen from groups of formula (I) and salts thereof:

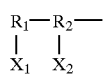
(I)

wherein:

$R_1$ is chosen from a carbonyl group and a thiocarbonyl group;

$R_2$ is chosen from CR groups wherein R is chosen from a direct bond to a neighboring atom, H, optionally substituted linear hydrocarbon groups, optionally substituted branched hydrocarbon groups, optionally substituted cyclic hydrocarbon groups, optionally substituted amino groups, optionally substituted thio groups, optionally substituted hydroxy groups, and halogen atoms;

$X_1$ is chosen from hydroxyl groups and thiol groups; and $X_2$ is chosen from hydroxyl groups, amino groups, and thiol groups, provided that said at least one complexing agent is not chosen from α-thio carboxylic acids.

2. A method according to claim 1, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable.

3. A method according to claim 2, wherein said at least one hydroxide compound is chosen from calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

4. A method according to claim 3, wherein said at least one hydroxide compound is calcium hydroxide.

5. A method according to claim 1, wherein said at least one hydroxide compound is present in an amount ranging from 0.1% to 10% by weight relative to the total weight of the at least one hydroxide composition.

6. A method according to claim 5, wherein said at least one hydroxide compound is present in an amount ranging from 2% to 5% by weight relative to the total weight of the at least one hydroxide composition.

7. A method according to claim 1, wherein said at least one activating composition further comprises at least one compound effective for forming at least one salt of said groups of formula (I).

8. A method according to claim 7, wherein said at least one compound effective for forming at least one salt of said groups of formula (I) is chosen from hydroxide compounds, which may be identical to or different from said at least one hydroxide compound.

9. A method according to claim 8, wherein at least one compound effective for forming at least one salt of said groups of formula (I) is sodium hydroxide.

10. A method according to claim 1, wherein said at least one activating composition further comprises at least one solvent.

11. A method according to claim 10, wherein said at least one solvent is chosen from water and organic solvents.

12. A method according to claim 10, wherein said at least one solvent is water.

13. A method according to claim 1, wherein said at least one activating composition is the form of a salt slurry.

14. A method according to claim 1, wherein said at least one complexing agent is chosen from mucic acid wherein said mucic acid is optionally substituted; homologs of mucic acid wherein said homologs of mucic acid are optionally substituted; derivatives of mucic acid wherein said derivatives of mucic acid are optionally substituted; and salts of any of the foregoing.

15. A method according to claim 1, wherein said keratin fibers are hair.

16. A method according to claim 1, further comprising rinsing said keratin fibers with water after said terminating of said lanthionization.

17. A method according to claim 1, wherein said lanthionization is terminated when a desired level of relaxation of the keratin fibers has been reached.

18. A method according to claim 1, wherein said dissociation is chosen from total dissociation and partial dissociation.

19. A method according to claim 1, wherein said salts of said groups of formula (I) are chosen from salts comprising organic cations and salts comprising inorganic cations.

20. A method according to claim 19, wherein said inorganic cations are chosen from sodium, lithium, and potassium.

21. A method according to claim 1, wherein said at least one hydroxide composition further comprises at least one suitable additive chosen from dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, and synthetic oils.

22. A composition comprising:

(a) at least one hydroxide compound; and (b) at least one complexing agent effective for dissociating said at least one hydroxide compound in sufficient quantity to effect lanthionization of keratin fibers, wherein said at least one complexing agent comprises at least one group chosen from groups of formula (I) and salts thereof:

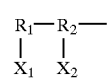
(I)

wherein:

$R_1$ is chosen from a carbonyl group and a thiocarbonyl group;

$R_2$ is chosen from CR groups wherein R is chosen from a direct bond to a neighboring atom, H, optionally substituted linear hydrocarbon groups, optionally substituted branched hydrocarbon groups, optionally substituted cyclic hydrocarbon groups, optionally substituted amino groups, optionally substituted thio groups, optionally substituted hydroxy groups, and halogen atoms;

$X_1$ is chosen from hydroxyl groups and thiol groups; and $X_2$ is chosen from hydroxyl groups, amino groups and thiol groups, provided that said at least one complexing agent is not chosen from α-thio carboxylic acids.

23. A composition according to claim 22, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable.

24. A composition according to claim 23, wherein said at least one hydroxide compound is chosen from calcium hydroxide, barium hydroxide, magnesium hydroxide, aluminum hydroxide, cupric hydroxide, strontium hydroxide, molybdenum hydroxide, manganese hydroxide, zinc hydroxide, and cobalt hydroxide.

25. A composition according to claim 24, wherein said at least one hydroxide compound is calcium hydroxide.

26. A composition according to claim 22, wherein said at least one hydroxide compound is present in an amount ranging from 0.1% to 10% by weight relative to the total weight of the at least one hydroxide composition.

27. A composition according to claim 26, wherein said at least one hydroxide compound is present in an amount ranging from 2% to 5% by weight relative to the total weight of the at least one hydroxide composition.

28. A composition according to claim 22, wherein said at least one complexing agent is chosen from mucic acid, optionally substituted; homologs of mucic acid, optionally substituted; derivatives of mucic acid, optionally substituted; and salts of any of the foregoing.

29. A composition according to claim 22, wherein said keratin fibers are hair.

30. A composition according to claim 22, wherein said dissociation is chosen from total dissociation and partial dissociation.

31. A composition according to claim 22, wherein said salts of said groups of formula (I) are chosen from salts comprising organic cations and salts comprising inorganic cations.

32. composition according to claim 31, wherein said inorganic cations are chosen from sodium, lithium, and potassium.

33. A composition according to claim 22, further comprising dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, and synthetic oils.

34. A composition according to claim 22, further comprising at least one solvent.

35. A composition according to claim 34, wherein said at least one solvent is chosen from water and DMSO.

36. A multicompartment kit comprising at least two compartments
wherein a first compartment comprises a first composition for generating hydroxide ions comprising at least one hydroxide compound; and
wherein a second compartment comprises an activating composition comprising at least one complexing agent effective for dissociating said at least one hydroxide compound in sufficient quantity to effect lanthionization of keratin fibers, wherein said at least one complexing agent comprises at least one group chosen from groups of formula (I) and salts thereof:

wherein:

$R_1$ is chosen from a carbonyl group and a thiocarbonyl group;

$R_2$ is chosen from CR groups wherein R is chosen from a direct bond to a neighboring atom, H, optionally substituted linear hydrocarbon groups, optionally substituted branched hydrocarbon groups, optionally substituted cyclic hydrocarbon groups, optionally substituted amino groups, optionally substituted thio groups, optionally substituted hydroxy groups, and halogen atoms;

$X_1$ is chosen from hydroxyl groups and thiol groups; and $X_2$ is chosen from hydroxyl groups, amino groups, and thiol groups. provided that said at least one complexing agent is not chosen from α-thio carboxylic acids.

* * * * *

UNITED STATES PATENT AND TRADEMARK OFFICE
CERTIFICATE OF CORRECTION

PATENT NO.    : 6,782,895 B2
DATED         : August 31, 2004
INVENTOR(S)   : Van Nguyen et al.

It is certified that error appears in the above-identified patent and that said Letters Patent is hereby corrected as shown below:

Column 12,
Line 6, "is the form" should read -- is in the form --.

Column 13,
Line 39, before "composition", insert -- A --.

Column 14,
Line 41, "groups." should read -- groups, --.

Signed and Sealed this

Eleventh Day of October, 2005

JON W. DUDAS
*Director of the United States Patent and Trademark Office*